(12) United States Patent
Roorda et al.

(10) Patent No.: US 7,807,210 B1
(45) Date of Patent: Oct. 5, 2010

(54) HEMOCOMPATIBLE POLYMERS ON HYDROPHOBIC POROUS POLYMERS

(75) Inventors: Wouter E. Roorda, Palo Alto, CA (US);
Niraj Shah, West New York, NJ (US);
André-Jean Lundkvist, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1191 days.

(21) Appl. No.: 10/818,927

(22) Filed: Apr. 5, 2004

Related U.S. Application Data (63) Continuation-in-part of application No. 09/704,212, filed on Oct. 31, 2000, now Pat. No. 6,833,153.

(51) Int. Cl.
*A61L 33/00* (2006.01)
*A61L 33/10* (2006.01)
*A61F 2/06* (2006.01)

(52) U.S. Cl. ............ 427/2.1; 427/2.24; 427/2.25; 623/1.43; 604/266

(58) Field of Classification Search .......... 427/2.1, 427/2.24, 2.25; 604/266
See application file for complete search history.

(56) References Cited

U.S. PATENT DOCUMENTS

| | | | | |
|---|---|---|---|---|
| 2,072,303 A | 3/1937 | Herrmann et al. | ........ | 128/335.5 |
| 2,386,454 A | 10/1945 | Frosch et al. | ................ | 260/78 |
| 3,773,737 A | 11/1973 | Goodman et al. | ............ | 260/78 |

(Continued)

FOREIGN PATENT DOCUMENTS

DE   42 24 401   1/1994

(Continued)

OTHER PUBLICATIONS

Anonymous, *Cardiologists Draw—Up the Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—Timothy H Meeks
*Assistant Examiner*—Cachet I Sellman
(74) *Attorney, Agent, or Firm*—Squire, Sanders & Dempsey L.L.P.

(57) ABSTRACT

The present invention relates to providing a porous, hydrophobic polymer with a hemocompatible substance and to the materials produced thereby. One embodiment of the present invention relates to the providing of expanded poly(tetrafluoroethylene) with one or more complexes of heparin, typically containing heparin in combination with a hydrophobic counter ion. The hemocompatible substance is dissolved in a mixture of solvents in which a first solvent wets the polymer to be coated and the second solvent enhances the solubility of the hemocompatible substance material in the solvent mixture. Typical first solvents wetting hydrophobic polymers include non-polar such as hydrochlorofluorocarbons. Typical second solvents include polar solvents such as organic alcohols and ketones. Azeotropic mixtures of the second solvent in the first solvent are used in some embodiments of the present invention although second solvents may be employed in a range of concentration ranges from less than 0.1% up to saturation. A typical example providing a heparin complex to an endoluminal stent, consisting of coating DURAFLO onto an ePTFE stent-covering material.

16 Claims, 4 Drawing Sheets

U.S. PATENT DOCUMENTS

| | | | | |
|---|---|---|---|---|
| 3,849,514 | A | 11/1974 | Gray, Jr. et al. | 260/857 |
| 3,953,566 | A | 4/1976 | Gore | 264/288 |
| 4,045,365 | A * | 8/1977 | Figiel | 510/178 |
| 4,118,485 | A * | 10/1978 | Eriksson et al. | 514/56 |
| 4,187,390 | A | 2/1980 | Gore | |
| 4,226,243 | A | 10/1980 | Shalaby et al. | 128/335.5 |
| 4,329,383 | A | 5/1982 | Joh | 428/36 |
| 4,343,931 | A | 8/1982 | Barrows | 528/291 |
| 4,529,792 | A | 7/1985 | Barrows | 528/291 |
| 4,531,916 | A | 7/1985 | Scantlebury et al. | 433/173 |
| 4,611,051 | A | 9/1986 | Hayes et al. | 528/295.3 |
| 4,654,327 | A | 3/1987 | Teng | 514/56 |
| 4,656,242 | A | 4/1987 | Swan et al. | 528/295.3 |
| 4,678,468 | A | 7/1987 | Hiroyoshi | 623/1 |
| 4,733,665 | A | 3/1988 | Palmaz | 128/343 |
| 4,745,105 | A | 5/1988 | Griffin et al. | |
| 4,745,107 | A | 5/1988 | Foley et al. | |
| 4,800,882 | A | 1/1989 | Gianturco | 128/343 |
| 4,871,357 | A * | 10/1989 | Hsu et al. | 604/266 |
| 4,882,168 | A | 11/1989 | Casey et al. | 424/468 |
| 4,886,062 | A | 12/1989 | Wiktor | 128/343 |
| 4,895,566 | A | 1/1990 | Lee | 604/266 |
| 4,931,287 | A | 6/1990 | Bae et al. | 424/484 |
| 4,941,870 | A | 7/1990 | Okada et al. | 600/36 |
| 4,977,901 | A | 12/1990 | Ofstead | 128/772 |
| 5,013,717 | A | 5/1991 | Solomon et al. | 514/56 |
| 5,019,096 | A | 5/1991 | Fox, Jr. et al. | 623/1 |
| 5,047,020 | A | 9/1991 | Hsu | 604/266 |
| 5,061,738 | A | 10/1991 | Solomon et al. | 523/100 |
| 5,069,899 | A | 12/1991 | Whitbourne et al. | |
| 5,073,265 | A * | 12/1991 | Johnson et al. | 210/500.23 |
| 5,100,992 | A | 3/1992 | Cohn et al. | 424/501 |
| 5,112,457 | A | 5/1992 | Marchant | 204/165 |
| 5,133,742 | A | 7/1992 | Pinchuk | 623/1 |
| 5,135,516 | A | 8/1992 | Sahatjian et al. | 604/265 |
| 5,163,952 | A | 11/1992 | Froix | 623/1 |
| 5,165,919 | A | 11/1992 | Sasaki et al. | 424/488 |
| 5,181,903 | A | 1/1993 | Vann et al. | 600/36 |
| 5,219,980 | A | 6/1993 | Swidler | 528/272 |
| 5,258,020 | A | 11/1993 | Froix | 623/1 |
| 5,272,012 | A | 12/1993 | Opolski | 428/423.1 |
| 5,292,516 | A | 3/1994 | Viegas et al. | 424/423 |
| 5,298,260 | A | 3/1994 | Viegas et al. | 424/486 |
| 5,300,295 | A | 4/1994 | Viegas et al. | 424/427 |
| 5,306,501 | A | 4/1994 | Viegas et al. | 424/423 |
| 5,306,786 | A | 4/1994 | Moens et al. | 525/437 |
| 5,322,659 | A | 6/1994 | Walder et al. | 264/171 |
| 5,328,471 | A | 7/1994 | Slepian | 604/101 |
| 5,330,768 | A | 7/1994 | Park et al. | 424/501 |
| 5,380,299 | A | 1/1995 | Fearnot et al. | 604/265 |
| 5,383,927 | A | 1/1995 | De Goicoechea et al. | 623/1 |
| 5,417,969 | A | 5/1995 | Hsu et al. | 424/78.27 |
| 5,417,981 | A | 5/1995 | Endo et al. | 424/486 |
| 5,441,759 | A | 8/1995 | Crouther et al. | 427/2.3 |
| 5,447,724 | A | 9/1995 | Helmus et al. | 424/426 |
| 5,455,040 | A | 10/1995 | Marchant | 424/426 |
| 5,462,990 | A | 10/1995 | Hubbell et al. | 525/54.1 |
| 5,464,650 | A | 11/1995 | Berg et al. | 427/2.3 |
| 5,485,496 | A | 1/1996 | Lee et al. | 378/64 |
| 5,516,881 | A | 5/1996 | Lee et al. | 528/320 |
| 5,525,348 | A | 6/1996 | Whitbourne et al. | 424/423 |
| 5,541,167 | A | 7/1996 | Hsu et al. | 514/56 |
| 5,569,463 | A | 10/1996 | Helmus et al. | 424/426 |
| 5,578,073 | A | 11/1996 | Haimovich et al. | 623/1 |
| 5,584,877 | A | 12/1996 | Miyake et al. | 623/1 |
| 5,605,696 | A | 2/1997 | Eury et al. | 424/423 |
| 5,607,467 | A | 3/1997 | Froix | 623/1 |
| 5,609,629 | A | 3/1997 | Fearnot et al. | 623/1 |
| 5,610,241 | A | 3/1997 | Lee et al. | 525/411 |
| 5,616,338 | A | 4/1997 | Fox, Jr. et al. | 424/423 |
| 5,624,411 | A | 4/1997 | Tuch | 604/265 |
| 5,628,730 | A | 5/1997 | Shapland et al. | 604/21 |
| 5,644,020 | A | 7/1997 | Timmermann et al. | 528/288 |
| 5,649,977 | A | 7/1997 | Campbell | 623/1 |
| 5,658,995 | A | 8/1997 | Kohn et al. | 525/432 |
| 5,667,767 | A | 9/1997 | Greff et al. | 424/9.411 |
| 5,670,558 | A | 9/1997 | Onishi et al. | 523/112 |
| 5,674,241 | A | 10/1997 | Bley et al. | 606/198 |
| 5,674,242 | A | 10/1997 | Phan et al. | 606/198 |
| 5,679,400 | A | 10/1997 | Tuch | 427/2.14 |
| 5,700,286 | A | 12/1997 | Tartaglia et al. | 623/1 |
| 5,702,754 | A | 12/1997 | Zhong | 427/2.12 |
| 5,711,958 | A | 1/1998 | Cohn et al. | 424/423 |
| 5,716,981 | A | 2/1998 | Hunter et al. | 514/449 |
| 5,721,131 | A | 2/1998 | Rudolph et al. | 435/240 |
| 5,723,219 | A | 3/1998 | Kolluri et al. | 428/411.1 |
| 5,735,897 | A | 4/1998 | Buirge | 623/12 |
| 5,746,998 | A | 5/1998 | Torchilin et al. | 424/9.4 |
| 5,759,205 | A | 6/1998 | Valentini | 623/16 |
| 5,776,184 | A | 7/1998 | Tuch | 623/1 |
| 5,783,657 | A | 7/1998 | Pavlin et al. | 528/310 |
| 5,788,979 | A | 8/1998 | Alt et al. | 424/426 |
| 5,800,392 | A | 9/1998 | Racchini | 604/96 |
| 5,820,917 | A | 10/1998 | Tuch | 427/2.1 |
| 5,824,048 | A | 10/1998 | Tuch | 623/1 |
| 5,824,049 | A | 10/1998 | Ragheb et al. | 623/1 |
| 5,830,178 | A | 11/1998 | Jones et al. | 604/49 |
| 5,837,008 | A | 11/1998 | Berg et al. | 623/1 |
| 5,837,313 | A | 11/1998 | Ding et al. | 427/2.21 |
| 5,849,859 | A | 12/1998 | Acemoglu | 528/271 |
| 5,851,508 | A | 12/1998 | Greff et al. | 424/9.411 |
| 5,854,376 | A | 12/1998 | Higashi | 528/288 |
| 5,858,746 | A | 1/1999 | Hubbell et al. | 435/177 |
| 5,865,814 | A | 2/1999 | Tuch | 604/265 |
| 5,869,127 | A | 2/1999 | Zhong | 427/2.12 |
| 5,873,904 | A | 2/1999 | Ragheb et al. | 623/1 |
| 5,876,433 | A | 3/1999 | Lunn | 623/1 |
| 5,877,224 | A | 3/1999 | Brocchini et al. | 514/772.2 |
| 5,879,697 | A | 3/1999 | Ding et al. | 424/422 |
| 5,879,713 | A | 3/1999 | Roth et al. | 424/489 |
| 5,902,875 | A | 5/1999 | Roby et al. | 528/310 |
| 5,905,168 | A | 5/1999 | Dos Santos et al. | 562/590 |
| 5,910,564 | A | 6/1999 | Gruning et al. | 528/310 |
| 5,914,182 | A * | 6/1999 | Drumheller | 428/308.4 |
| 5,914,387 | A | 6/1999 | Roby et al. | 528/310 |
| 5,919,893 | A | 7/1999 | Roby et al. | 525/411 |
| 5,925,720 | A | 7/1999 | Kataoka et al. | 525/523 |
| 5,932,299 | A | 8/1999 | Katoot | 427/508 |
| 5,955,016 | A | 9/1999 | Goldfarb | 264/127 |
| 5,955,509 | A | 9/1999 | Webber et al. | 514/772.7 |
| 5,955,588 | A | 9/1999 | Tsang et al. | |
| 5,958,385 | A | 9/1999 | Tondeur et al. | 424/61 |
| 5,958,638 | A * | 9/1999 | Katayama et al. | 430/65 |
| 5,962,138 | A | 10/1999 | Kolluri et al. | 428/411.1 |
| 5,968,070 | A | 10/1999 | Bley et al. | 606/198 |
| 5,971,954 | A | 10/1999 | Conway et al. | 604/96 |
| 5,980,928 | A | 11/1999 | Terry | 424/427 |
| 5,980,972 | A | 11/1999 | Ding | 427/2.24 |
| 5,993,489 | A | 11/1999 | Lewis et al. | 628/1 |
| 5,993,890 | A | 11/1999 | Marchant et al. | 427/2.3 |
| 5,997,517 | A | 12/1999 | Whitbourne | 604/265 |
| 6,010,530 | A | 1/2000 | Goicoechea | 623/1 |
| 6,011,125 | A | 1/2000 | Lohmeijer et al. | 525/440 |
| 6,015,541 | A | 1/2000 | Greff et al. | 424/1.25 |
| 6,033,582 | A | 3/2000 | Lee et al. | 216/37 |
| 6,034,204 | A | 3/2000 | Mohr et al. | 528/328 |
| 6,042,875 | A | 3/2000 | Ding et al. | 427/2.24 |
| 6,048,484 | A | 4/2000 | House et al. | 264/322 |
| 6,051,576 | A | 4/2000 | Ashton et al. | 514/255 |
| 6,051,648 | A | 4/2000 | Rhee et al. | 525/54.1 |
| 6,054,553 | A | 4/2000 | Groth et al. | 528/335 |
| 6,056,993 | A | 5/2000 | Leidner et al. | 427/2.25 |
| 6,060,451 | A | 5/2000 | DiMaio et al. | 514/13 |
| 6,060,518 | A | 5/2000 | Kabanov et al. | 514/781 |

| Patent # | Type | Date | Inventor | Class |
|---|---|---|---|---|
| 6,080,488 | A | 6/2000 | Hostettler et al. | 428/423.3 |
| 6,090,134 | A | 7/2000 | Tu et al. | 623/1 |
| 6,096,027 | A | 8/2000 | Layne | |
| 6,096,070 | A | 8/2000 | Ragheb et al. | 623/1 |
| 6,099,562 | A | 8/2000 | Ding et al. | 623/1.46 |
| 6,110,188 | A | 8/2000 | Narciso, Jr. | 606/153 |
| 6,110,483 | A | 8/2000 | Whitbourne et al. | 424/423 |
| 6,113,629 | A | 9/2000 | Ken | 23/1.1 |
| 6,120,491 | A | 9/2000 | Kohn et al. | 604/502 |
| 6,120,536 | A | 9/2000 | Ding et al. | 623/1.43 |
| 6,120,788 | A | 9/2000 | Barrows | 424/426 |
| 6,120,904 | A | 9/2000 | Hostettler et al. | 428/423.3 |
| 6,121,027 | A | 9/2000 | Clapper et al. | 435/180 |
| 6,129,761 | A | 10/2000 | Hubbell | 623/11 |
| 6,136,333 | A | 10/2000 | Cohn et al. | 424/423 |
| 6,143,354 | A | 11/2000 | Koulik et al. | 427/2.24 |
| 6,153,252 | A | 11/2000 | Hossainy et al. | 427/2.3 |
| 6,159,978 | A | 12/2000 | Myers et al. | 514/252.1 |
| 6,165,212 | A | 12/2000 | Dereume et al. | 623/1.13 |
| 6,172,167 | B1 | 1/2001 | Stapert et al. | 525/420 |
| 6,177,523 | B1 | 1/2001 | Reich et al. | 525/459 |
| 6,180,632 | B1 | 1/2001 | Myers et al. | 514/252.1 |
| 6,203,551 | B1 | 3/2001 | Wu | 6/108 |
| 6,211,249 | B1 | 4/2001 | Cohn et al. | 514/772.1 |
| 6,214,901 | B1 | 4/2001 | Chudzik et al. | 523/113 |
| 6,231,600 | B1 | 5/2001 | Zhong | 623/1.42 |
| 6,240,616 | B1 | 6/2001 | Yan | 29/527.2 |
| 6,241,710 | B1* | 6/2001 | VanTassel et al. | 604/272 |
| 6,245,753 | B1 | 6/2001 | Byun et al. | 514/56 |
| 6,245,760 | B1 | 6/2001 | He et al. | 514/234.8 |
| 6,248,129 | B1 | 6/2001 | Froix | 623/1.42 |
| 6,251,136 | B1 | 6/2001 | Guruwaiya et al. | 623/1.46 |
| 6,254,632 | B1 | 7/2001 | Wu et al. | 623/1.15 |
| 6,255,027 | B1* | 7/2001 | Wehelie et al. | 430/65 |
| 6,258,121 | B1 | 7/2001 | Yang et al. | 623/1.46 |
| 6,258,371 | B1 | 7/2001 | Koulik et al. | 424/422 |
| 6,262,034 | B1 | 7/2001 | Mathiowitz et al. | 514/44 |
| 6,270,788 | B1 | 8/2001 | Koulik et al. | 424/423 |
| 6,277,449 | B1 | 8/2001 | Kolluri et al. | 427/289 |
| 6,283,947 | B1 | 9/2001 | Mirzaee | 604/264 |
| 6,283,949 | B1 | 9/2001 | Roorda | 604/288.02 |
| 6,284,305 | B1 | 9/2001 | Ding et al. | 427/2.28 |
| 6,287,628 | B1 | 9/2001 | Hossainy et al. | 427/2.3 |
| 6,299,604 | B1 | 10/2001 | Ragheb et al. | 604/264 |
| 6,306,176 | B1 | 10/2001 | Whitbourne | 623/23.59 |
| 6,331,313 | B1 | 12/2001 | Wong et al. | 424/427 |
| 6,335,029 | B1 | 1/2002 | Kamath et al. | 424/423 |
| 6,344,035 | B1 | 2/2002 | Chudzik et al. | 604/265 |
| 6,346,110 | B2 | 2/2002 | Wu | 6/108 |
| 6,358,556 | B1 | 3/2002 | Ding et al. | 427/2.24 |
| 6,379,381 | B1 | 4/2002 | Hossainy et al. | 623/1.42 |
| 6,387,379 | B1 | 5/2002 | Goldberg et al. | 424/400 |
| 6,395,326 | B1 | 5/2002 | Castro et al. | 427/2.24 |
| 6,417,153 | B1* | 7/2002 | Owens | 510/411 |
| 6,419,692 | B1 | 7/2002 | Yang et al. | 623/1.15 |
| 6,451,373 | B1 | 9/2002 | Hossainy et al. | 427/2.25 |
| 6,482,834 | B2 | 11/2002 | Spada et al. | 514/311 |
| 6,494,862 | B1 | 12/2002 | Ray et al. | 604/96.01 |
| 6,503,538 | B1 | 1/2003 | Chu et al. | 424/497 |
| 6,503,556 | B2 | 1/2003 | Harish et al. | 427/2.24 |
| 6,503,954 | B1 | 1/2003 | Bhat et al. | 514/772.2 |
| 6,506,437 | B1 | 1/2003 | Harish et al. | 427/2.25 |
| 6,524,347 | B1 | 2/2003 | Myers et al. | |
| 6,527,801 | B1 | 3/2003 | Dutta | 623/1.46 |
| 6,527,863 | B1 | 3/2003 | Pacetti et al. | 118/500 |
| 6,528,526 | B1 | 3/2003 | Myers et al. | 214/311 |
| 6,530,950 | B1 | 3/2003 | Alvarado et al. | 623/1.13 |
| 6,530,951 | B1 | 3/2003 | Bates et al. | 623/1.45 |
| 6,540,776 | B2 | 4/2003 | Sanders Millare et al. | 623/1.15 |
| 6,544,223 | B1 | 4/2003 | Kokish | 604/103.01 |
| 6,544,543 | B1 | 4/2003 | Mandrusov et al. | 424/422 |
| 6,544,582 | B1 | 4/2003 | Yoe | 27/2.24 |
| 6,555,157 | B1 | 4/2003 | Hossainy | 427/2.24 |
| 6,558,733 | B1 | 5/2003 | Hossainy et al. | 427/2.24 |
| 6,565,659 | B1 | 5/2003 | Pacetti et al. | 118/500 |
| 6,572,644 | B1 | 6/2003 | Moein | 623/1.11 |
| 6,585,755 | B2 | 7/2003 | Jackson et al. | 623/1.15 |
| 6,585,765 | B1 | 7/2003 | Hossainy et al. | 623/1.45 |
| 6,585,926 | B1 | 7/2003 | Mirzaee | 264/400 |
| 6,605,154 | B1 | 8/2003 | Villareal | 118/500 |
| 6,616,765 | B1 | 9/2003 | Hossaony et al. | 623/1.45 |
| 6,623,448 | B2 | 9/2003 | Slater | 604/95.01 |
| 6,625,486 | B2 | 9/2003 | Lundkvist et al. | 604/21 |
| 6,645,135 | B1 | 11/2003 | Bhat | 600/3 |
| 6,645,195 | B1 | 11/2003 | Bhat et al. | 604/528 |
| 6,656,216 | B1 | 12/2003 | Hossainy et al. | 623/1.13 |
| 6,656,506 | B1 | 12/2003 | Wu et al. | 424/489 |
| 6,660,034 | B1 | 12/2003 | Mandrusov et al. | 623/1.42 |
| 6,663,662 | B2 | 12/2003 | Pacetti et al. | 623/1.13 |
| 6,663,880 | B1 | 12/2003 | Roorda et al. | 424/423 |
| 6,666,880 | B1 | 12/2003 | Chiu et al. | 623/1.11 |
| 6,673,154 | B1 | 1/2004 | Pacetti et al. | 118/500 |
| 6,673,385 | B1 | 1/2004 | Ding et al. | 427/2.28 |
| 6,689,099 | B2 | 2/2004 | Mirzaee | 604/107 |
| 6,695,920 | B1 | 2/2004 | Pacetti et al. | 118/500 |
| 6,706,013 | B1 | 3/2004 | Bhat et al. | 604/96.01 |
| 6,709,514 | B1 | 3/2004 | Hossainy | 118/52 |
| 6,712,845 | B2 | 3/2004 | Hossainy | 623/1.42 |
| 6,713,119 | B2 | 3/2004 | Hossainy et al. | 427/2.25 |
| 6,716,444 | B1 | 4/2004 | Castro et al. | 424/422 |
| 6,723,120 | B2 | 4/2004 | Yan | 623/1.15 |
| 6,733,768 | B2 | 5/2004 | Hossainy et al. | 424/426 |
| 6,740,040 | B1 | 5/2004 | Mandrusov et al. | 600/439 |
| 6,743,462 | B1 | 6/2004 | Pacetti | 427/2.24 |
| 6,749,626 | B1 | 6/2004 | Bhat | 623/1.1 |
| 6,753,071 | B1 | 6/2004 | Pacetti et al. | 428/212 |
| 6,758,859 | B1 | 7/2004 | Dang et al. | 623/1.15 |
| 6,759,054 | B2 | 7/2004 | Chen et al. | 424/423 |
| 6,764,505 | B1 | 7/2004 | Hossainy et al. | 623/1.15 |
| 2001/0007083 | A1 | 7/2001 | Roorda | 623/1.15 |
| 2001/0014717 | A1 | 8/2001 | Hossainy et al. | 525/60 |
| 2001/0018469 | A1 | 8/2001 | Chen et al. | 523/121 |
| 2001/0020011 | A1 | 9/2001 | Mathiowitz et al. | 514/44 |
| 2001/0029351 | A1 | 10/2001 | Falotico et al. | 604/103.02 |
| 2001/0037145 | A1 | 11/2001 | Guruwaiya et al. | 623/1.15 |
| 2001/0051608 | A1 | 12/2001 | Mathiowitz et al. | 514/44 |
| 2002/0005206 | A1 | 1/2002 | Falotico et al. | 128/898 |
| 2002/0007213 | A1 | 1/2002 | Falotico et al. | 623/1.21 |
| 2002/0007214 | A1 | 1/2002 | Falotico | 623/1.21 |
| 2002/0007215 | A1 | 1/2002 | Falotico et al. | 623/1.21 |
| 2002/0009604 | A1 | 1/2002 | Zamora et al. | 428/450 |
| 2002/0016625 | A1 | 2/2002 | Falotico et al. | 623/1.13 |
| 2002/0032414 | A1 | 3/2002 | Ragheb et al. | 604/265 |
| 2002/0032434 | A1 | 3/2002 | Chudzik et al. | 604/890.1 |
| 2002/0051730 | A1 | 5/2002 | Bodnar et al. | 422/33 |
| 2002/0071822 | A1 | 6/2002 | Uhrich | 424/78.37 |
| 2002/0077693 | A1 | 6/2002 | Barclay et al. | 623/1.13 |
| 2002/0082679 | A1 | 6/2002 | Sirhan et al. | 623/1.15 |
| 2002/0087123 | A1 | 7/2002 | Hossainy et al. | 604/198 |
| 2002/0091433 | A1 | 7/2002 | Ding et al. | 623/1.2 |
| 2002/0094440 | A1 | 7/2002 | Llanos et al. | 428/421 |
| 2002/0111590 | A1 | 8/2002 | Davila et al. | 604/265 |
| 2002/0120326 | A1 | 8/2002 | Michal | 623/1.15 |
| 2002/0123801 | A1 | 9/2002 | Pacetti et al. | 623/1.46 |
| 2002/0142039 | A1 | 10/2002 | Claude | 424/486 |
| 2002/0155212 | A1 | 10/2002 | Hossainy | 427/2.25 |
| 2002/0165608 | A1 | 11/2002 | Llanos et al. | 623/1.45 |
| 2002/0176849 | A1 | 11/2002 | Slepian | 424/93.7 |
| 2002/0183581 | A1 | 12/2002 | Yoe et al. | 600/3 |
| 2002/0188037 | A1 | 12/2002 | Chudzik et al. | 523/112 |
| 2002/0188277 | A1 | 12/2002 | Roorda et al. | 604/523 |
| 2003/0004141 | A1 | 1/2003 | Brown | 514/152 |
| 2003/0028243 | A1 | 2/2003 | Bates et al. | 623/1.15 |
| 2003/0028244 | A1 | 2/2003 | Bates et al. | 623/1.15 |
| 2003/0031780 | A1 | 2/2003 | Chudzik et al. | 427/2.1 |
| 2003/0032767 | A1 | 2/2003 | Tada et al. | 528/310 |

| | | | |
|---|---|---|---|
| 2003/0036794 A1 | 2/2003 | Ragheb et al. ............. 623/1.15 |
| 2003/0039689 A1 | 2/2003 | Chen et al. .................. 424/468 |
| 2003/0040712 A1 | 2/2003 | Ray et al. .................... 604/173 |
| 2003/0040790 A1 | 2/2003 | Furst ......................... 623/1.11 |
| 2003/0059520 A1 | 3/2003 | Chen et al. ................... 427/2.1 |
| 2003/0060877 A1 | 3/2003 | Falotico et al. ............. 623/1.42 |
| 2003/0065377 A1 | 4/2003 | Davila et al. ............... 623/1.13 |
| 2003/0072868 A1 | 4/2003 | Harish et al. ............... 427/2.24 |
| 2003/0073961 A1 | 4/2003 | Happ ........................ 604/274 |
| 2003/0083646 A1 | 5/2003 | Sirhan et al. ............. 604/891.1 |
| 2003/0083739 A1 | 5/2003 | Cafferata ................... 623/1.42 |
| 2003/0097088 A1 | 5/2003 | Pacetti ......................... 604/19 |
| 2003/0097173 A1 | 5/2003 | Dutta ........................ 623/1.38 |
| 2003/0099712 A1 | 5/2003 | Jayaraman .................. 424/486 |
| 2003/0105518 A1 | 6/2003 | Dutta ........................ 623/1.38 |
| 2003/0113439 A1 | 6/2003 | Pacetti et al. ............... 427/2.24 |
| 2003/0150380 A1 | 8/2003 | Yoe ............................ 118/423 |
| 2003/0157241 A1 | 8/2003 | Hossainy et al. ........... 427/2.24 |
| 2003/0158517 A1 | 8/2003 | Kokish .................. 604/103.01 |
| 2003/0190406 A1 | 10/2003 | Hossainy et al. ........... 427/2.25 |
| 2003/0207020 A1 | 11/2003 | Villareal .................... 427/2.24 |
| 2003/0211230 A1 | 11/2003 | Pacetti et al. ............... 427/2.24 |
| 2004/0018296 A1 | 1/2004 | Castro et al. ............... 427/2.25 |
| 2004/0029952 A1 | 2/2004 | Chen et al. ................... 514/449 |
| 2004/0047978 A1 | 3/2004 | Hossainy et al. ............ 427/2.1 |
| 2004/0047980 A1 | 3/2004 | Pacetti et al. ............... 427/2.25 |
| 2004/0052858 A1 | 3/2004 | Wu et al. .................... 424/490 |
| 2004/0052859 A1 | 3/2004 | Wu et al. .................... 424/490 |
| 2004/0054104 A1 | 3/2004 | Pacetti ........................ 526/242 |
| 2004/0060508 A1 | 4/2004 | Pacetti et al. ............... 118/264 |
| 2004/0062853 A1 | 4/2004 | Pacetti et al. ................ 427/2.1 |
| 2004/0063805 A1 | 4/2004 | Pacetti et al. ............... 523/113 |
| 2004/0071861 A1 | 4/2004 | Mandrusov et al. ........ 427/2.24 |
| 2004/0072922 A1 | 4/2004 | Hossainy et al. ........... 523/113 |
| 2004/0073298 A1 | 4/2004 | Hossainy .................. 623/1.46 |
| 2004/0086542 A1 | 5/2004 | Hossainy et al. ........... 424/423 |
| 2004/0086550 A1 | 5/2004 | Roorda et al. .............. 424/448 |
| 2004/0096504 A1 | 5/2004 | Michal ....................... 424/471 |
| 2004/0098117 A1 | 5/2004 | Hossainy et al. ........... 623/1.42 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 03173838 A * | 7/1991 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |

OTHER PUBLICATIONS

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ: 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis($\alpha$-amino acid)$\alpha,\omega$-Alkylene Diesters, and Aliphatic Dicarboxylic Acids*, Journal of Polymer Science, Part A: Polymer Chemistry, 37(4), 391-407 (1999).

Levy et al, *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising $\alpha$-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*, Chemical Abstract 125:212307 (1996).

Silver et al., *Biomaterials Science and Biocompatibility*, Springer-Verlag, pp. 1-26 (1999).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

\* cited by examiner

HEMOCOMPATIBLE POLYMERS ON HYDROPHOBIC POROUS POLYMERS

REFERENCE TO RELATED APPLICATIONS

This application is a Continuation-in-Part application from U.S. application Ser. No. 09/704,212, Hemocompatible Coatings on Hydrophobic Porous Polymers, filed 31 Oct. 2000, now U.S. Pat. No. 6,833,153, and hereby claims priority to that application.

BACKGROUND

1. Field of the Invention

The present invention relates to the field of hemocompatible polymers on hydrophobic porous polymeric materials and, in particular, to hemocompatible substances based upon complexes of heparin deposited upon porous hydrophobic polymers, typically expanded PTFE.

2. Description of Related Art

Continuing advances in medical technology have led to the development and use of numerous medical devices that come into contact with blood or other bodily fluids. To be concrete in our discussion, we focus herein on the particular example of medical devices coming into contact with mammalian blood, particularly human blood, not intending thereby to limit the scope of the present invention to medical devices used exclusively on human patients. In using such devices, it is important that contact of the blood or other bodily fluid with the various components of the medical device not cause therapeutically detrimental alterations to the fluid. In many cases, it is desirable to coat such devices with materials to enhance the biocompatibility of the devices, including coatings that contain bioactive agents, anticoagulants, antimicrobial agents or a variety of other drugs.

It is convenient to consider blood-contacting medical devices as invasive or extra-corporal, although some devices span both classes. Invasive devices are used internally in the treatment of the patient, implanted into the patient for an indefinite or extended period of time or inserted into the patient for relatively brief periods. In many cases, the materials comprising the blood-contacting portions of the invasive device lack sufficient biocompatibility and/or hemocompatibility. This tends to cause changes harmful to the patient in the blood or other fluid coming into contact with the surface (or surfaces) of the device. In such cases it is desirable to coat the surfaces of these devices with materials to enhance the biocompatibility and/or hemocompatibility. Invasive devices that are typically coated with biocompatible or therapeutic substances include implantable artificial orthopedic devices, dental implants, intravascular catheters, emboli capturing systems, epicardial immobilization devices, grafts, stents, intraluminal prosthetic devices and artificial heart valves, among others.

There are also many examples of extra-corporal medical devices that come into contact with blood in which blood is transported and/or processed external to the patient. A few representative examples include cardiopulmonary bypass devices, kidney dialysis equipment, blood oxygenators, separators and defoaming devices, among others. Following such extra-corporal processing, the blood or other bodily fluid may be reintroduced into the patient, transported for storage and/or introduced into another patient. In using such extra-corporal devices, it is important that contact of the blood or other bodily fluid with the various components of the device not cause therapeutically detrimental alterations to the fluid.

It is important in some cases that the surface or the surfaces of the invasive or extra-corporal medical device be coated with substances having therapeutic functions, wherein the coatings may serve several functions in addition to increasing the biocompatibility/hemocompatibility of the surface. Examples of such additional functions include the release of one or more therapeutic agents into the blood in appropriate dosages with appropriate timed-released characteristics and at the proper location within the patient. Thus, the medical device may serve as a convenient delivery platform for the delivery of therapeutically beneficial drugs in addition to its other functions.

One important application related to implantable devices arises in connection with endoluminal stents, particularly as occurring in connection with percutaneous transluminal angioplasty ("PCTA"). Following balloon angioplasty, the lumen of the just-expanded vessel may contract due to several causes. An initial rebound of the walls of the vessel may occur following removal of the balloon. Further thrombosis or restenosis of the blood vessel may occur over time following the angioplasty procedure. The result is often the necessity for another angioplasty procedure or surgical by-pass. Endoluminal stents have been in use for several years in conjunction with a surgical procedure inserting a tube or stent into the vessel following the PCTA procedure to assist in retaining the desired intraluminal opening. A review of the procedure may be found in *Endoluminal Stenting* by Ulrich Sigwart, Ed. (W. B. Saunders, 1996). A compendium of coronary stents is given in *Handbook of Coronary Stents*, $3^{rd}$ Ed. by P. W. Serruys and M. J B Kutryk, Eds. (Martin Dunitz Ltd., 2000). However, even with stenting, occlusions frequently recur within the stent requiring further PCTA or by-pass surgery. Such restenosis following PCTA and the insertion of a stent is sought to be prevented by the use of coated stents. Coatings on stents are often used for the delivery of anticoagulants or other medication that assist in preventing thrombosis and restenosis.

Heparin is an anticoagulant drug composed of a highly sulfated polysaccharide, the principle constituent of which is a glycosaminoglycan. In combination with a protein cofactor, heparin acts as an antithrombin (among other medical effects as described, for example, in *Heparin-Binding Proteins*, by H. B. Conrad (Academic Press, 1998)). Heparin is an attractive additive to coat on the surface(s) of blood-contacting devices in order to increase the hemocompatibility of the material and/or to release heparin or heparin complexes into the blood to combat thrombosis and restenosis.

The heparin molecule contains numerous hydrophilic groups including hydroxyl, carboxyl, sulfate and sulfamino making underivatized heparin difficult to coat onto hydrophobic polymers. Thus, many types of complexes of heparin with hydrophobic counter ions have been used in order to increase the ability of the heparin-counter ion complex to bind to hydrophobic surfaces. Such counter ions are typically cationic to facilitate binding with anionic heparin, and contain a hydrophobic region to facilitate bonding with the hydrophobic polymer. Typical heparin complexes include, but are not limited to, heparin complex with typically large quaternary ammonium species such as benzylalkonium groups (typically introduced in the form of benzylalkonium chloride), tridodecylmethylammonium chloride ("TDMEC"), and the commercial heparin complex offered by Baxter International under the tradename DURAFLO or DURAFLO II. Herein we denote as "heparin complex" any complex of heparin with a hydrophobic counter ion, typically a relatively large counter ion. Examples of heparin complexes are described in the following U.S. Pat. Nos. 4,654,327; 4,871,357; 5,047,020;

5,069,899; 5,525,348; 5,541,167 (incorporated herein by reference) and references cited therein.

Considerable work has been done in developing coatings for application to various medical devices in which the coatings contain at least one form of heparin or heparin complex. Combinations of heparin and heparin complexes with other drugs, as well as various techniques for tailoring the coating to provide desired drug-release characteristics have been studied. Examples of such work include that of Chen et. al. (incorporated herein by reference), published in J. Vascular Surgery, Vol 22, No. 3 pp 237-247 (September 1995) and the following U.S. Pat. Nos. 4,118,485; 4,678,468; 4,745,105; 4,745,107; 4,895,566; 5,013,717; 5,061,738; 5,135,516; 5,322,659; 5,383,927; 5,417,969; 5,441,759; 5,865,814; 5,876,433; 5,879,697; 5,993,890 (incorporated herein by reference) as well as references cited in the foregoing patents and article, such cited references hereby incorporated a reference into this document.

Implantable medical devices often require some degree of porosity to enable blood to come into contact with underlying tissues, to increase the surface area for delivery of therapeutic substances, or for other purposes. Therefore, porous polymers are widely used in medical devices. The advantages of porosity are not limited to implantable devices, and porous materials are used in extra-corporal devices as well as invasive medical devices. However, the problem of coating with heparin is exacerbated if the hydrophobic polymer is also porous. In addition to binding with the hydrophobic surface, the heparin complex must also penetrate into the interstices of the porous structure of the polymer and bind to all or substantially all of the polymer surface that comes into contact with blood.

Fluorinated polymers are typically chemically unreactive, have low surface energy and are hydrophobic. Such properties are generally favorable for use in medical devices as described, for example by F. H. Silver and D. L. Christiansen in *Biomaterials Science and Biocompatibility*, (Springer-Verlag, 1999) p. 19. Poly(tetrafluoroethylene), PTFE, is a polymeric material with repeating units of ($-CF_2CF_2-$) having numerous commercial uses, including in blood-contacting devices, due in large part to its chemical inertness and desirable physical properties. PTFE in the form of a film or solid has low surface energy and, therefore, is a relatively difficult surface to coat (or "wet"). "Wetting" typically indicates the tendency of a liquid to spread and coat the surface onto which it is placed. The specific relationship between surface energy and the contact angle at the interface between a drop and the surface (the "wetting") is given in standard references including *Physical Chemistry of Surfaces* $6^{th}$ *Ed.* by A. W. Adams and A. P. Gast (John Wiley, 1997), p. 465 ff. A contact angle between the liquid and the surface greater than approximately 90° typically indicates a non-wetting liquid on that particular surface.

In many medical and non-medical commercial uses, it is desirable to have PTFE in the form of a porous film that retains adequate physical strength for the particular application while not substantially increasing the cost of the material. Expanded PTFE (hereinafter "ePTFE") is a form of PTFE that has been physically expanded along one or more directions to create a porous form of PTFE having varying amounts of porosity depending on several factors including the specific procedures for performing the mechanical expansion. The porous ePTFE thus created is useful for the manufacture of several commercial products as illustrated (for example) by the work of Gore in U.S. Pat. Nos. 3,953,566 and 4,187,390 and the work of House et. al. in U.S. Pat. No. 6,048,484. Applications to stents include the work of Lewis et. al. (U.S. Pat. No. 5,993,489) and Bley et. al. (U.S. Pat. Nos. 5,674,241 and 5,968,070). The chemical inactivity, and other properties of fluorinated polymers including PTPE and ePTFE, have made them attractive substances for use in many medical and blood-contacting devices. Representative examples include dental implant devices (Scantlebury et. al. U.S. Pat. No. 4,531,916), grafts, stents and intraluminal prosthetic devices (Bley et. al. U.S. Pat. Nos. 5,674,241 and 5,968, 070; Goldfarb et. al. U.S. Pat. No. 5,955,016; Lewis et. al. U.S. Pat. No. 5,993,489; Tu et. al. U.S. Pat. No. 6,090,134).

Expanded PTFE is widely used in medical devices and is perhaps one of the most widely used vascular graft materials. In fact, ePTFE has a large range of application in blood-contacting medical devices including, but not limited to, segmental venous replacements, reconstructed veins in organ transplantation, polymer catheters, in-dwelling catheters, urological and coronary stents, covered stents, heart valves, dental implants, orthopedic devices, vascular grafts, synthetic by-pass grafts and other invasive and implantable medical devices. In addition, ePTFE can be used in extra-corporal blood-contacting devices. Examples include, but are not limited to, heart by-pass devices, kidney dialysis equipment, blood oxygenators, defoaming machines, among others.

Figure 1:
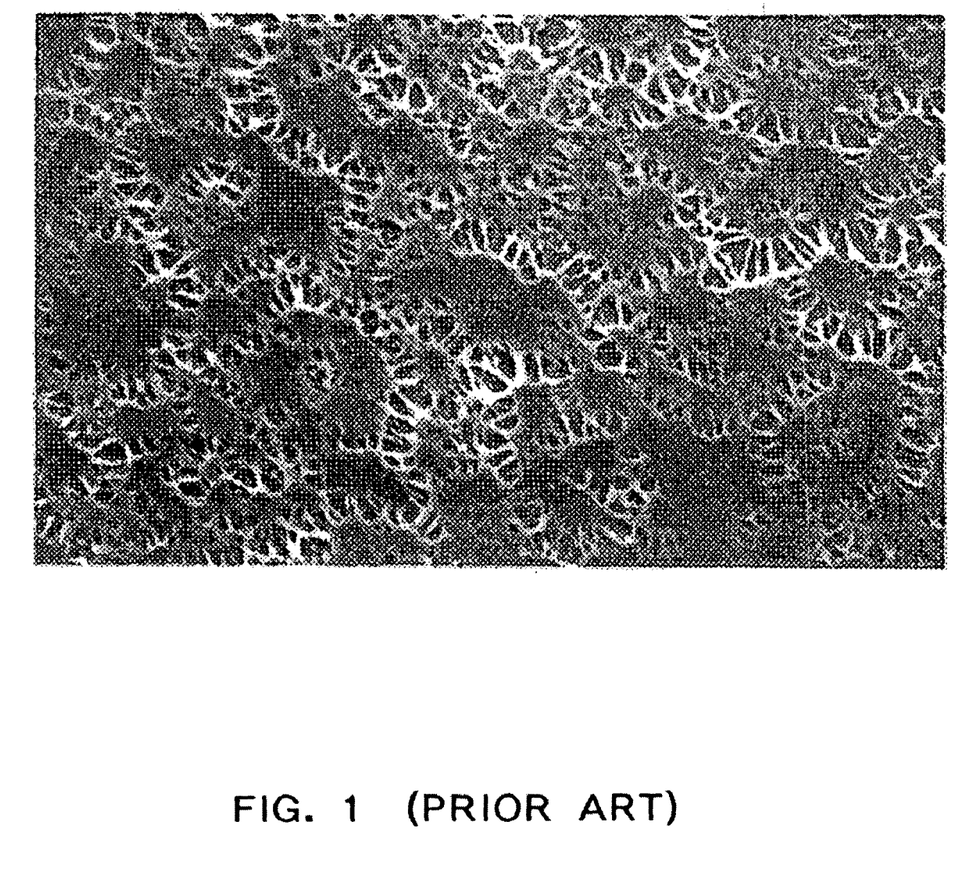
FIG. 1: Scanning electron micrograph of ePTFE from U.S. Pat. No. 6,048,484.
Figure 2A:
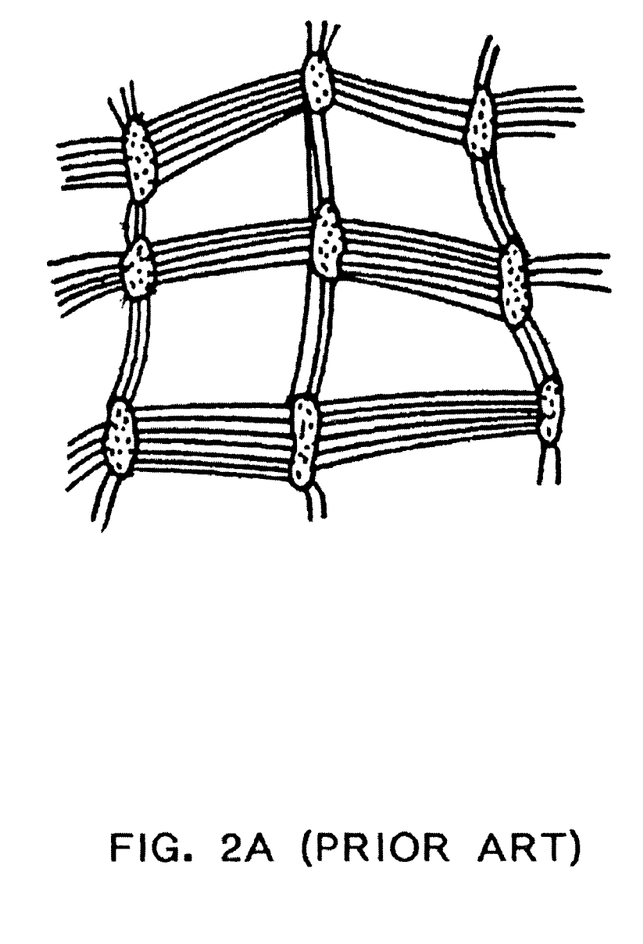
FIG. 2A: Schematic depiction of porous structure of ePTFE from U.S. Pat. No. 6,048,484 depicting biaxially oriented fibrils.
Figure 2B:
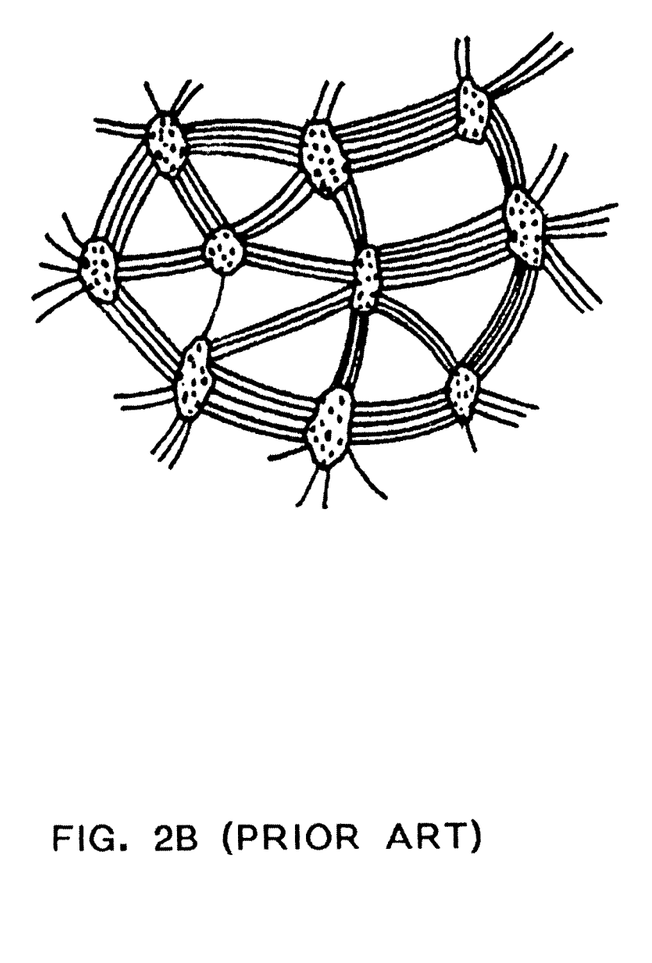
FIG. 2B: Schematic depiction of porous structure of ePTFE from U.S. Pat. No. 6,048,484 depicting multiaxially oriented fibrils.

FIG. 1 is a scanning electron micrograph of porous ePTFE from the work of House et. al. (U.S. Pat. No. 6,048,484). FIGS. 2A and 2B are schematic depictions of two forms of ePTFE showing biaxially oriented fibrils (FIG. 2A), and multiaxially oriented fibrils (FIG. 2B). Both FIGS. 2A and 2B are from House et. al. (supra). Low surface energy characteristic of fluoropolymers and other hydrophobic polymers, in combination with the porosity of ePTFE, make the application of a coating to ePTFE, including coating of the interior surfaces of the pores, a significant challenge. Providing such a coating for ePTFE is one objective of the present invention.

However, when used in a blood-contacting environment, ePTFE tends to be thrombogenic and its porosity may release entrapped gases (which may itself be a source of thrombogenicity as discussed, for example, by Vaun et. al. U.S. Pat. No. 5,181,903). Therefore, considerable effort has gone into the coating of ePTFE to reduce its thrombogenicity and/or provide other therapeutic effects. Hemocompatibility can be achieved by a variety of means, including coating with a hydrophilic, biologically passive, polymer, or by coating with materials having a biologically active component such as heparin or a complex of heparin including the commercially available heparin complex DURAFLO or DURAFLO II (Baxter Healthcare, Inc.). Improved procedures for coating ePTFE with hemocompatible substances, typically substances containing derivatives or complexes of heparin, and the improved hemocompatible materials so produced are among the objects of the present invention. We use the expressions "derivative of heparin" and "complex of heparin" interchangeably herein without distinction to indicate a chemical combination of heparin with a counter ion.

Although fluoropolymers have been among the most commonly used materials for blood-contacting devices, polyurethanes, polyethylene terephthalates ("PETs") and numerous other fluorinated and non-fluorinated polymers have also found considerable application. Modifications of polyurethanes, PETs and other plastics have included the introduction of coatings for antithrombogenic and anticoagulant properties. PET is an example of a non-fluorinated polymer that is highly hydrophobic and therefore difficult to coat with polar, aqueous materials such as heparin. PTFE is but one example of the general chemical class of fluoropolymer that also includes FEP (fluorinated ethylene propylene), PFA (perfluoroalkyl vinyl ether and tetrafluoroethylene co-polymer), PVDF (polyvinylidenedifluoride), PVF (polyvinylfluoride), PCTFE (polychlorotrifluoroethylene), ETFE (ethylene and tetrafluoroethylene co-polymer) TFB (terpolymer of vinylidenedifluoride, hexafluoropropylene and tetrafluoroethylene) and other fluoropolymers as known in the art and described in many references including, for example, W. Woebcken in *Saechtling International Plastics Handbook for the Technologist, Engineer and User*, $3^{rd}$ Ed., (Hanser Publishers, 1995) pp. 234-240, incorporated herein by reference.

Coating the interior regions of highly porous materials such as ePTFE with significant amounts of a hemocompatible substances presents special challenges in addition to the hydrophobicity, deriving in part from the relative inaccessibility of much of the surface to be coated.

SUMMARY

The present invention relates to methods of providing porous, hydrophobic polymers with a hemocompatible substance, to the materials produced thereby and to medical devices in which at least a portion of the blood-contacting surfaces thereof comprise such hemocompatible materials. One embodiment of the present invention relates to the coating of expanded poly(tetrafluoroethylene), ePTFE, with one or more complexes containing heparin bonded to a hydrophobic counter ion. The porous nature of ePTFE makes penetration and coating of the interior regions of the material difficult due to surface tension effects, entrapped gases and similar phenomena characteristic of liquid penetration into porous structures. Such porosity-related challenges to coating are exacerbated by the low surface energy of PTFE. The present invention makes use of a solvent that both penetrates the porous regions of ePTFE and dissolves heparin complexes. Solvents used pursuant to the present invention include nonpolar solvents that wet PTFE.

A hemocompatible substance is dissolved in a mixture of solvents in which a first solvent wets the polymer to be coated and the second solvent enhances the solubility of the hemocompatible substance material in the solvent mixture. First solvents that have the property of wetting hydrophobic polymers are typically nonpolar. Typical second solvents include polar solvents such as organic alcohols, ketones, among other possibilities. In one embodiment, azeotropic mixtures of the second solvent in the first solvent are used, although concentrations of the second solvent from near zero up to saturation may be used. The present invention also relates to medical devices, including endoluminal stents, that employ the coated materials of the present invention. Producing a porous material having a hemocompatible substance on at least some blood-contacting surfaces thereof is a primary object of the present invention. Medical devices using such materials in a blood-contacting environment have the advantages of reducing the accumulation of platelets and thrombus on the coated surfaces.

DETAILED DESCRIPTION

The present invention relates to the coating of porous, hydrophobic polymers, typically fluoropolymers such as expanded poly(tetrafluoroethylene), ePTFE, with hemocompatible substances, so as to perfuse and coat substantially all regions of the surface that come into contact with blood, including the interior regions of the porous structure that are difficult to access and difficult to coat by conventional means. Complexes of heparin are the typical hemocompatible substances employed in some embodiments of the present invention.

We follow the conventional usage that "wetting" indicates that the contact angle formed by the tangent to the surface of the liquid and the surface of the solid at the point of contact is less than 90° (measured through the liquid phase) such that the liquid tends to spread over the surface of the solid. Conversely, nonwetting indicates that the liquid tends to ball up on the surface of the solid and run off the surface easily. Contact angles are known in the art and provide one criteria by which candidate solvents of the present invention can be identified. For example, contact angles of selected liquids with selected surfaces (including fluoropolymers such as PTFE, FEP) are provided in *Physical Chemistry of Surfaces* $6^{th}$ Ed. (supra) pp. 365-366.

The present invention is not inherently limited to ePTFE or to fluoropolymers as a class. Porous hydrophobic polymeric materials, that are typically difficult to coat with hemocompatible materials by procedures of the prior art are included within the scope of the present invention. Examples of porous hydrophobic polymers include the following: porous polyethylene, porous polypropylene, porous polyurethanes, porous polyacrylates, porous polymethacrylates, among others. Biocompatible polyurethanes, PETs and other polymers have also been used as blood-contacting substances in medical devices, subject to coating with heparin complexes and/or other hemocompatible or therapeutic molecules pursuant to the methods of the present invention. However, PTFE is but one example of a class of commercially important fluoropolymers. Other examples include those noted above; FEP, PFA, PVDF, PVF, PCTFE, ETFE, TFB and other fluoropolymers as known in the art. Blends containing ePTFE, other fluoropolymers and/or other hydrophobic polymers are included within the scope of the present invention. Such blends are coatable by means of the procedures described herein and the resulting coated materials are useful in blood-contacting medical devices.

To be concrete in our discussions we describe in detail the particular embodiments in which expanded PTFE is coated with a hemocompatible substance containing heparin as one component thereof. Other embodiments making use of other porous hydrophobic polymers and/or other hemocompatible substances consistent with the procedures and conditions of the present invention represent obvious modifications of the present invention and are included within its scope. Some embodiments specifically exclude subjecting the hemocompatible substance to a dialdehyde cross-linking or dialdehyde stabilization step before in vivo use.

The present invention relates to coating ePTFE without distinction as to the particular microstructure present in the ePTFE prior to coating. Herein we use "ePTFE" to indicate any porous structure of the PTFE polymer, irrespective of its specific and detailed microstructure and irrespective of the detailed procedure for its formation. Commercially available embodiments of ePTFE such as GORE-TEX (W. L. Gore and Associates) are included. In some embodiments of the present invention, mechanically expansion of PTFE is the means by which porosity is obtained. However, as described by Gore (U.S. Pat. Nos. 3,953,566 and 4,187,390, incorporated herein by reference), mechanical expansion is not the only way to obtain porous PTFE. The coating procedures of the present invention can be used for coating porous polymeric materials, including ePTFE, irrespective of the specific mechanism by which the porosity is introduced into the material. However, for economy of language, we use "ePTFE" to denote a porous form of PTFE, however produced, recognizing that mechanically expanded PTFE is but one means of obtaining the desired porosity.

Liquids having contact angles with PTFE less than 90° include non-polar organic solvents such as alkanes (pentane, hexane, heptane and octane, among others) and cycloalkanes, freons or related materials such as chlorofluorocarbons ("CFCs") and hydrochlorofluorocarbons ("HCFCs"). Commercial solvents include CFCs and HCFCs such as "Techspray AMS Flux Remover" (from Techspray, Inc., of Amarillo, Tex.) and "Gensolv 2004" (from Micro Care Corp. of Bristol, Conn.). Various ethers, tetrahydrofuran, dioxane are among the solvents wetting PTFE. For some embodiments of the present invention, a candidate solvent is any solvent that is known to wet fluoropolymers (particularly ePTFE) or the hydrophobic polymer of interest. Although pure solvents are discussed herein, this is merely for economy of language. Mixtures of solvents that retain the property of being able to wet the hydrophobic surface, particularly ePTFE, are included within the scope of the present invention.

Some invention embodiments specifically exclude solvent mixtures that comprise more than 10 weight percent, more than 20 weight percent, more than 30 weight percent, or more than 40 weight percent of a mixture of trifluoro trichloro ethanes.

A hydrophobic complex of heparin is dissolved in the polymer-wetting primary solvent for penetration into the porous structure and deposition onto ePTFE in some embodiments of the present invention. Some (typically small) amount of heparin complex dissolves in pure polymer-wetting solvent as described above, but typically does not lead to biologically useful amounts of heparin being deposited onto the hydrophobic surfaces. Therefore, in some embodiments of the present invention, the solubility of heparin complexes is enhanced by the addition of relatively small amounts of a polar solvent to the non-polar primary solvent. The non-polar primary solvent is chosen to provide adequate penetration into the interior of the porous hydrophobic material, while the polar solubility-enhancing component of the solvent is selected to facilitate dissolution of heparin complexes in the solvent mixture. Candidate polar solubility-enhancing additives included organic alcohols (methanol, ethanol, among others), ketones (acetone, methylethylketone, among others). Mixtures of one or more chemical compounds can also be used as the solubility-enhancing solvent.

In some embodiments, the solubility-enhancing component is limited to solvents or solvent mixtures that have at least the following two characteristics. First, the hemocompatible substance is more soluble in the solubility-enhancing component than the substance is in the polymer-wetting primary solvent. Second, the hemocompatible substance is more soluble in the solubility-enhancing component than it is in a mixture of the polymer-wetting primary solvent and the solubility-enhancing component. Such solubility-enhancing components are said to be particularly solubility enhancing.

Some invention embodiments specifically exclude solvent mixtures that comprise more than 1 weight percent, more than 2 weight percent, more than 3 weight percent, more than 4 weight percent, more than 5 weight percent, more than 10 weight percent, more than 20 weight percent, more than 30 weight percent, or more than 40 weight percent of ethanol.

It is desirable, but not inherently necessary in some embodiments of the present invention, that the polar solvent be added to the non-polar solvent in an amount so as to form an azeotropic mixture. Azeotropic mixtures have the property of evaporating such that the unevaporated liquid retains the same composition to dryness. In contrast, non-azeotropic mixtures typically become more concentrated in the less volatile solvent as evaporation proceeds. A solute will thus experience a changing solvent composition during evaporation for non-azeotropic mixtures. This may lead to precipitation of the solute and tend to create non-uniform coatings. Thus, while non-azeotropic mixtures may be used with acceptable results, azeotropic mixtures typically give better coatings.

One example of a substantially azeotropic mixture described in detail below includes a polymer-wetting solvent HCFC-225 containing about 6% methanol (by volume). This solvent mixture is found to be adequate in the some embodiments of the present invention. "HCFC-225" is a mixture of isomers of dichloropentafluoropropane, typically HCFC-225ca is $CF_3CF_2CHCl_2$ and HCFC225cb is $CClF_2CF_2CHFCl$. However, azeotropic mixtures are not necessary in the present invention and adequate results are obtained with concentrations of polar solvent from approximately 0.00001% up to saturation of the polar solvent dissolved in the non-polar solvent. In some embodiments of the present invention, concentrations of polar solvent in the range from about 0.1% to about 10% by volume are used. However, while the above ranges give therapeutically useful amounts of hemocompatible substances, better quality coatings are typically obtained with concentrations in the range from approximately 0.1% to approximately 2%. A range from approximately 0.5% to approximately 1% is particularly useful in that 0.5% has enough hemocompatible material for therapeutically effective coatings by 1% is dilute enough to avoid webbing.

Thus, the present invention includes adding relatively small amounts of an organic alcohol (such as ethanol, methanol, among others) or a similar solubility-enhancing polar solvent to a polymer-wetting solvent. The solubility enhancing solvent is added to the polymer-wetting solvent in such quantity (typically small) that the mixed solvent provides adequate solubility for heparin complexes without substantially hindering penetration of the pores or wetting of the hydrophobic polymer. Thus, in one embodiment a mixed solvent is created that both wets ePTFE and delivers heparin to all surfaces of the porous structure.

Having dissolved a suitable heparin complex in a mixed solvent as described herein, coating of the ePTFE with the heparin complex may be performed by any convenient method that brings the heparin-containing solution into intimate contact with all surface regions of the ePTFE substrate including the interior regions of the pores. Dip coating is one technique that can be used in some embodiments of the present invention although other coating techniques known in the art may also be used, including spraying.

Figure 3:
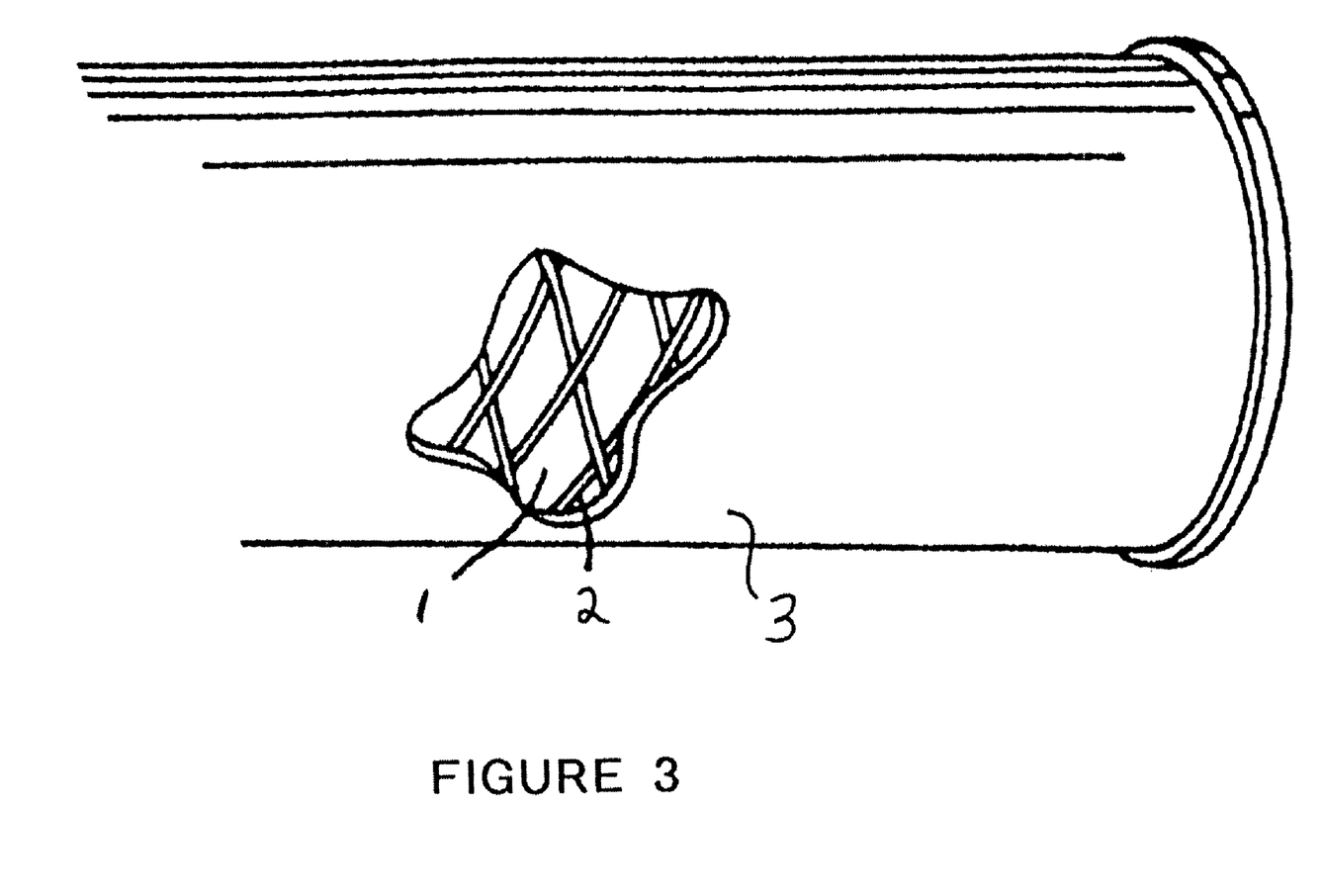
FIG. 3: Cut-away depiction of a portion of a covered stent.

FIG. 3 depicts a portion of an endoluminal stent in cutaway view, showing the interior region of the stent, 1, the struts, 2, and a covering, 3. The covering material for the stent, 3, is typically porous to allow blood flowing on the interior of the stent, 1, to come into contact with the interior surfaces of the lumen in which the stent is placed. Porous materials containing hemocompatible substances thereon may be used in many medical devices, one example of which is stent covering, 3. Expanded PTFE is a typical stent covering material. Other materials for covering stents are described elsewhere herein and in the references cited.

Hemocompatible substances placed onto stent cover, 3, include heparin and heparin complexes. One embodiment of the present invention relates to coating a ePTFE stent covering material with a heparin complex, typically DURAFLO or DURAFLO II. Typical pore sizes of ePTFE are in the range of approximately 5 μm (microns) to approximately 200 μm, commonly in the range from approximately 40 μm to approximately 120 μm.

EXAMPLES

DURAFLO II may be used herein in place of DURAFLO without modification.
1) Prepare a solution consisting of the hydrochlorofluorocarbon HCFC-225 and 6% by volume methanol whereby the methanol enhances the solubility of the heparin complex in the HCFC solvent.
2) Dissolve in the solution of step 1, a heparin complex, DURAFLO. The concentration of DURAFLO in the solution is selected to provide the desired coating of DURAFLO on the stent cover. Too little drug on the stent cover may be therapeutically ineffective. Too much may cause excess amounts of drug to be released into the blood soon after the stent is implanted, to the detriment of the patient.
3) Dip ePTFE into the solution of step 2 allowing the solution to perfuse throughout the ePTFE porosity and deposit the DURAFLO throughout.
4) Repeat step 3 if additional coating of DURAFLO is desired.

Other solvents that may be used in step 1 above include the following:
1-a) Techspray AMS Flux Remover containing approximately 6% methanol.
1-b) Genesolv 2004, dichlorofluoroethane containing approximately 4% methanol.
1-c) Cyclohexane including approximately 5% n-propanol.

Other solutes that may be used in step 2 above include the following:
2-a) TDMEC heparin.
2-b) Benzalkonium heparin.

Concentrations of solute in solvent may be any convenient value leading to the appropriate deposition of hemocompatible substance onto the surface of the polymer. Typical concentrations in the range of approximately 1%-3% are found to give adequate coatings.

The material produced by the above procedure is a suitable stent covering material containing DURAFLO (or other heparin complex) coated on substantially all surfaces thereof that will be exposed to blood during use. Dip or spray coating is conveniently done on a porous, hydrophobic polymer already mounted on the struts, forming thereby a stent covering. However, the hydrophobic, porous material may be coated pursuant to the present invention before, during or following the fabrication of the material into a medical device. The timing of coating and device fabrication is determined in part by manufacturing considerations including the damage likely to result to the hemocompatible substance by processing during device fabrication.

The properties of the coating can be tested in vitro by standard testing methods including AT-III binding or anti-Factor Xa Assay. Other biological assays include various ex vivo shunts.

This application hereby incorporated by reference the entire specification and claims of parent application, U.S. application Ser. No. 09/704,212.

Having described the invention in detail, those skilled in the art will appreciate that, given the present disclosure, modifications may be made to the invention without departing from the spirit of the inventive concept described herein. Therefore, it is not intended that the scope of the invention be limited to the specific embodiments illustrated and described.

We claim:

1. A method comprising:
providing a medical device comprising a porous hydrophobic polymer substrate,
providing a hemocompatible substance,
preparing an azeotropic solution comprising the hemocompatible substance and an azeotropic mixture of:
a first solvent that wets the porous hydrophobic polymer substrate;
a second solvent that enhances the solubility of the hemocompatible substance in the azeotropic solution; and
depositing the hemocompatible substance onto the porous hydrophobic polymer substrate by contacting the porous hydrophobic polymer substrate with the azeotropic solution,
wherein the first solvent of the azeotropic mixture is trichloro trifluoro ethanes, and the amount of the trichloro trifluoro ethanes in the azeotropic mixture is 10 wt % or less.

2. The method of claim 1 wherein the porous hydrophobic polymer substrate composes a blood-contacting component of a medical device.

3. The method of claim 2 wherein the medical device is a stent.

4. The method of claim 1 wherein the porous hydrophobic polymer substrate includes at least one polymer material selected from the group consisting of porous polyethylene materials, porous polypropylene materials, porous polyurethane materials, porous polyacrylate materials, porous polymethacrylate materials and porous fluoropolymer materials.

5. The method of claim 4 wherein the porous fluoropolymer material comprises an expanded poly(tetrafluoroethylene) material.

6. The method of claim 1 wherein the hemocompatible substance comprises ionic heparin and a hydrophobic counter ion.

7. The method of claim 6 wherein the hydrophobic counter ion is a hydrophobic quaternary ammonium ion.

8. The method of claim 6 wherein the hydrophobic counter ion is one or more of benzylalkonium ion and tridodecylmethylammonium ion.

9. The method of claim 1 wherein the second solvent is one or more of organic alcohols, and ketones.

10. The method of claim 1 wherein the amount of the second solvent dissolved in the first solvent is from about 0.00001% by weight up to the saturation point of the second solvent in the first solvent.

11. The method of claim 10 wherein the amount of the second solvent mixed in the first solvent is from about 0.1 to about 10% by weight.

12. The method of claim 11 wherein the amount of the second solvent mixed in the first solvent is from about 0.1 to about 2% by weight.

13. The method of claim 12 wherein the amount of the second solvent mixed in the first solvent is from about 0.5 to about 1% by weight.

14. The method of claim 1 wherein the hemocompatible substance is deposited on the hydrophobic polymer substrate by dipping.

15. A method comprising:
    providing a medical device comprising a porous hydrophobic polymer substrate,
    providing a hemocompatible substance,
    preparing an azeotropic solution comprising a mixture of:
        a first solvent that wets the porous hydrophobic polymer substrate;
        a second solvent that enhances the solubility of the hemocompatible substance in the solution, wherein the second solvent and the first solvent form an azeotropic mixture; and
        the hemocompatible substance; and
    depositing the hemocompatible substance onto the porous hydrophobic polymer substrate by contacting the porous hydrophobic polymer substrate with the azeotropic solution,
    provided that the hemocompatible substance is not subjected to a dialdehyde cross-linking or dialdehyde stabilization step before in vivo use, wherein the first solvent is a mixture of isomers of dichloropentafluoropropanes, the second solvent is methanol, and the first solvent and second solvent are mixed to form a 6% solution by weight.

16. A method comprising:
    providing a medical device comprising a porous hydrophobic polymer substrate,
    providing a hemocompatible substance,
    preparing an azeotropic solution comprising a mixture of:
        a first solvent that wets the porous hydrophobic polymer substrate;
        a second solvent that enhances the solubility of the hemocompatible substance in the solution, wherein the second solvent and the first solvent form an azeotropic mixture; and
        the hemocompatible substance; and
    depositing the hemocompatible substance onto the porous hydrophobic polymer substrate by contacting the porous hydrophobic polymer substrate with the azeotropic solution,
    provided that the hemocompatible substance is not subjected to a dialdehyde cross-linking or dialdehyde stabilization step before in vivo use, wherein the first solvent is cyclohexane, the second solvent is n-propanal, and the first solvent and second solvent are mixed to form a 5% solution by weight.

* * * * *